(12) United States Patent
Friedman

(10) Patent No.: US 6,918,144 B2
(45) Date of Patent: Jul. 19, 2005

(54) SELF-HEATING PORTABLE MASSAGE TABLE

(76) Inventor: Michael Friedman, 6430 N. Hamlin Ave., Lincolnwood, IL (US) 60712

( * ) Notice: Subject to any disclaimer, the term of this patent is extended or adjusted under 35 U.S.C. 154(b) by 8 days.

(21) Appl. No.: 10/407,982

(22) Filed: Apr. 4, 2003

(65) Prior Publication Data

US 2004/0194211 A1 Oct. 7, 2004

(51) Int. Cl.$^7$ .......................... A61G 13/00; A61F 7/00; A61F 7/12
(52) U.S. Cl. ................ 5/620; 5/421; 607/98; 108/50.13; 219/217
(58) Field of Search ................ 5/620, 421; 607/98, 607/81; 108/50.13; 219/217

(56) References Cited

U.S. PATENT DOCUMENTS

| | | | | | |
|---|---|---|---|---|---|
| 2,184,418 A | * | 12/1939 | Faigle | ........................ | 607/81 |
| 3,136,577 A | * | 6/1964 | Richard | .................. | 297/180.11 |
| 3,924,284 A | * | 12/1975 | Nelson | ........................ | 219/217 |
| 4,162,393 A | * | 7/1979 | Balboni | ....................... | 219/217 |
| 4,607,624 A | * | 8/1986 | Jefferson | ...................... | 601/18 |
| 4,868,898 A | * | 9/1989 | Seto | ........................... | 219/528 |
| 4,943,041 A | * | 7/1990 | Romein | ........................ | 5/620 |
| 2002/0019654 A1 | * | 2/2002 | Ellis et al. | .................... | 607/98 |

* cited by examiner

*Primary Examiner*—Alexander Grosz
(74) *Attorney, Agent, or Firm*—Holland & Knight LLP; Todd S. Parkhurst

(57) ABSTRACT

A self-heating, portable massage or therapy table is disclosed. The portable massage table comprises a cushioned pad that is comfortable for a user to sit or lie on. Preferably inside the cushioned pad is an electrical heat mechanism which heats the cushioned pad. The cushioned pad and the heat mechanisms are sectioned so that the surface can be folded. Finally, the table comprises foldable legs that support the table.

2 Claims, 3 Drawing Sheets

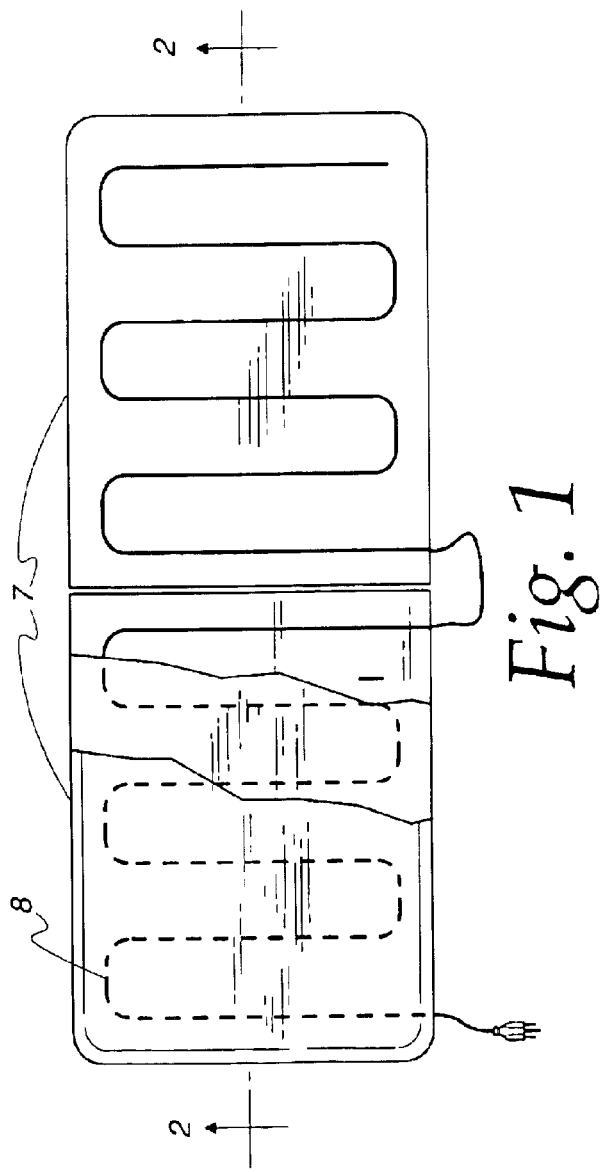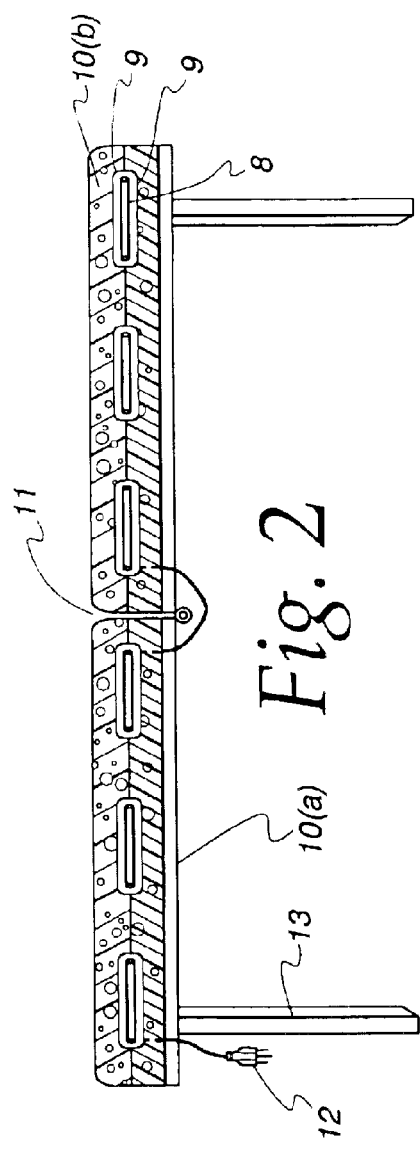

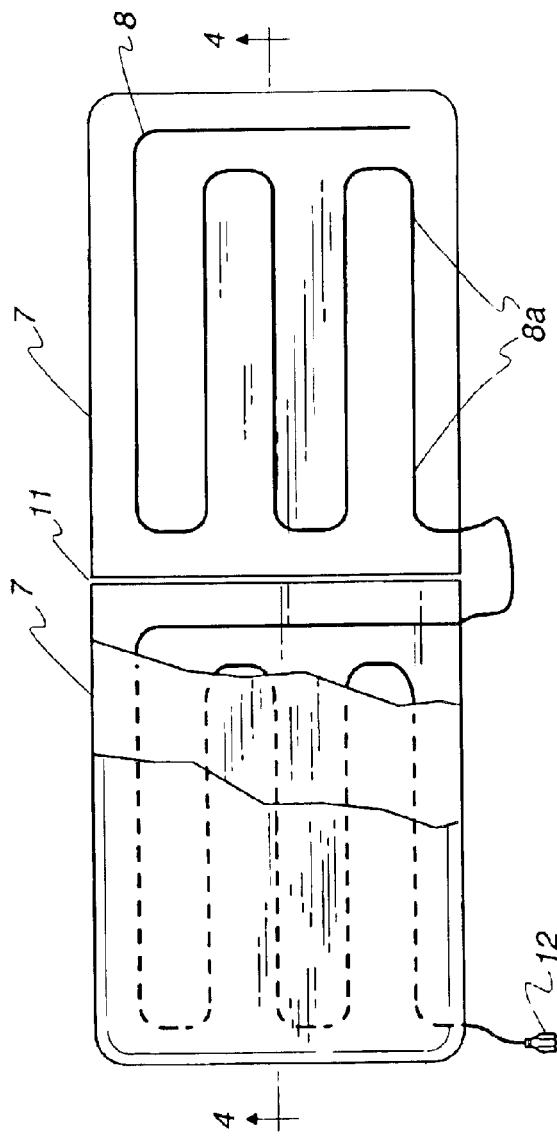
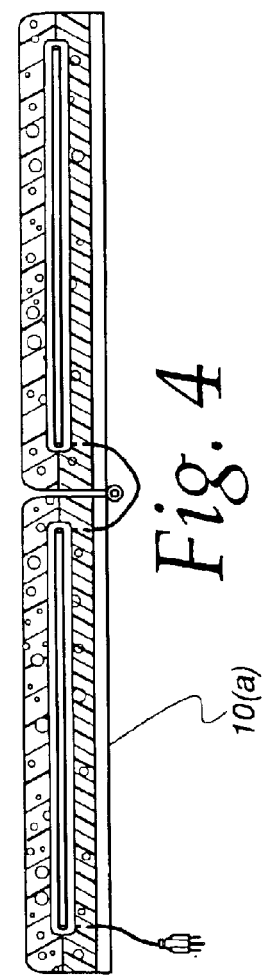

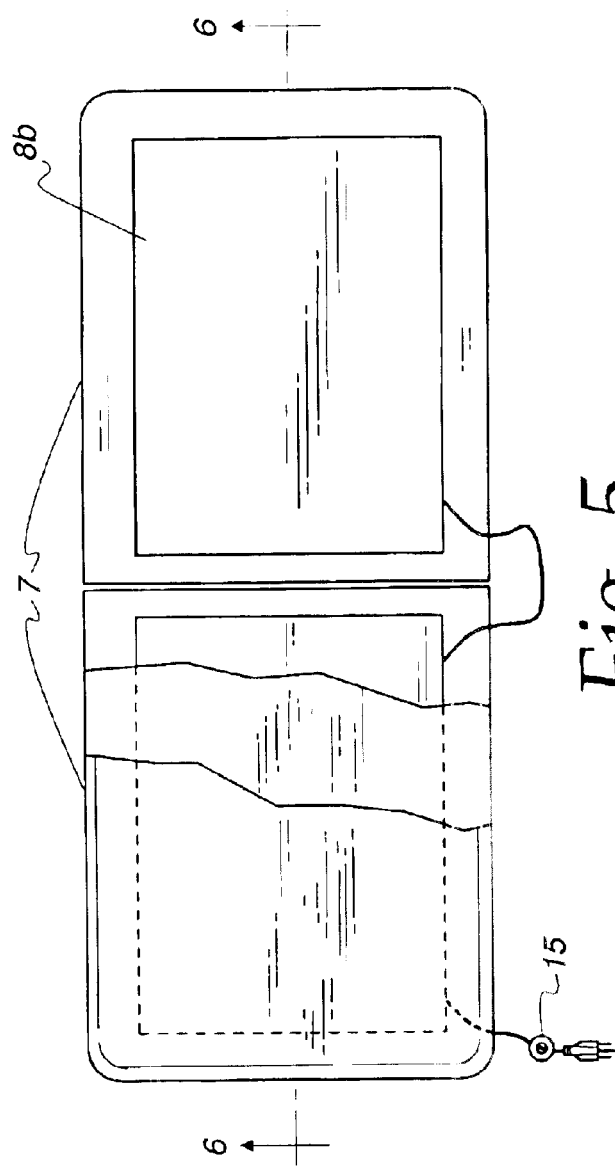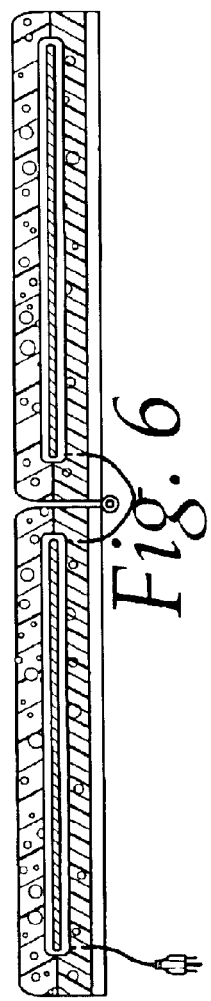

SELF-HEATING PORTABLE MASSAGE TABLE

TECHNICAL FIELD OF THE INVENTION

The present invention relates, in general, to the field of massage or therapy tables and, in particular, to a portable massage or therapy table that is self-heated.

BACKGROUND OF THE INVENTION

Portable massage tables are well known in the prior art. Portable tables comprise a sectioned mattress with a bendable base and folding legs. As such, they are well suited for masseuses and therapists who serve clients at various locations.

However, such tables lack a desirable feature; that feature is heat. Heat relaxes the body and mind, reduces stress levels and relaxes tight muscles. Heat is also therapeutic because it makes joints more flexible, soothes backaches, stimulates circulation and relieves pain related to arthritis and rheumatism.

Despite these benefits, heat is not incorporated into current portable massage tables. Masseuses and therapists heat conventional tables using separate heating pads and warm towels. Under these conventional heating methods, heat is lost after a heating pad is turned off while a person is placed on the table or when the towels themselves get cold. Although a heating pad can be utilized while the table is in use, a therapist or masseuse must take care to maintain a comfortable temperature for the human body. To this extent, they may need to add another heat insulation layer on top of the heating pad or remove it entirely from the table. Either solution results in wasted time, discomfort for the table user and loss of heat. Additionally, separate heating pads add extra expense and increase travel weight of the table, thereby decreasing the benefits of portable tables. Finally, heating pads become dangerous when worn thin after frequent use.

Existing self-heated tables utilize water (hydrotherapy tables) and light bulbs to provide the necessary heat. Such tables are primarily directed toward surgical purposes and other stationary contexts. As a result, they are bulky, extremely heavy and expensive. Moreover, special safety concerns also arise from these heat sources. For example, hydrotherapy tables require special water compartments that are resistant to damage and leaks. In addition, damaged light bulbs can cut or electrocute a user.

The present invention discloses a system which solves or at least substantially reduces the impact of these problems associated with existing portable massage tables.

It is one object and advantage of the present invention to provide a self-heated, portable massage table.

It is another object and advantage of the present invention to provide a portable massage table that includes all of the benefits of heat during massage or therapy or any other use.

It is still another object and advantage of the present invention to provide a self-heated portable massage table that provides consistent heat.

It is an additional object and advantage of the present invention to provide a portable massage table that allows control over the table temperature.

It is yet another object and advantage of the present invention to provide a self-heated portable massage table that is safe for regular use.

It is further an object and advantage of the present invention to provide a self-heated portable massage table that is transportable and inexpensive.

The above and other objects, advantages and features of the present invention will become more readily appreciated and understood from a consideration of the following detailed description of preferred embodiments of the present invention when taken together with the accompanying drawings of the present invention.

SUMMARY OF THE INVENTION

In accordance with the foregoing objects, the present invention comprises a surface with a cushioned pad, an insulated electrical heating mechanism within the cushioned pad, and folding legs.

BRIEF DESCRIPTION OF THE DRAWINGS

The following figures are schematic representations of the invention:

FIG. 1—is a top plan view of the heated massage table showing one embodiment of the electrical heat mechanism;

FIG. 2—is a sectional view of the cushioned pad with the electrical heat mechanism, the view being taken in the plane of line 2—2 in FIG. 1;

FIG. 3—is a top plan view of the heated massage table showing another embodiment of the electrical heat mechanism;

FIG. 4—is a sectional view of the cushioned pad with the other embodiment of the electrical heat mechanism, the view being taken in the plane of line 4—4 in FIG. 3;

FIG. 5—is a top plan view of the heated massage table showing a third embodiment of the electrical heat mechanism;

FIG. 6—is a sectional view of the cushioned pad with the third embodiment of the electrical heat mechanism, the view being taken in the plane of line 6—6 in FIG. 5.

DETAILED DESCRIPTION OF THE INVENTION

While various embodiments of the present invention are discussed in detail below, it should be appreciated that the present invention provides inventive concepts that can be embodied in a wide variety of specific contexts. The specific embodiments discussed are merely illustrative of specific ways to make and use the invention, and do not limit the scope of the invention.

Turning first to FIG. 1, there is shown a cushioned pad 7 that provides the contact surface for the user. For example, a user may comfortably sit or lie on a surface of the cushioned pad 7. The cushioned pad 7 can be supported on a rigid plywood or similarly rigid planar surface 10(a). In addition, there is shown an electrical heat mechanism 8 which heats the cushioned pad 7 thereby heating the portable massage or therapy table. In the preferred embodiment of the invention, the electrical heat mechanism is placed substantially in the middle of the cushioned pad 7. (See FIG. 2). However, the electrical heat mechanism can be placed at various locations within the cushioned pad 7.

FIG. 2 shows a side elevational view of the cushioned pad 7 with insulation 9 around the electrical heat mechanism 8 and cushion material 10(b). The insulation protects the surrounding areas of the cushioned pad and a user from electrical damage as well as damage from excessive heat. In addition, the electrical heat mechanism is preferably placed a sufficient distance away from the surface of the cushioned pad 7 within the cushion material 10(a) so that a consistent heat is provided to the entire surface. Various materials may be used for cushion such as mattress springs, foam, cotton, feathers, etc.

Furthermore, the figure displays that in the preferred embodiment the cushioned pad 7 has a separation 11 which allows the cushioned pad to be folded in half. However, any section scheme and various hinges or other mechanisms may be utilized in order to allow the portable table to fold. In addition, there is shown an electrical plug 12 that is used to power and heat the electrical heat mechanism 8. Although a plug that can be inserted into any commercial socket is shown, various other sources of power such as battery packs and other electrical power sources may be used. Finally, FIG. 2 also shows foldable legs 13 of the portable massage table. The foldable legs 13 support the table while in use and fold under the cushioned pad 7 during transport.

FIG. 3 shows an alternate pattern 8*a* for the placement of the electrical heat mechanism 8. FIG. 4 provides a side elevational view of the cushioned pad 7 with the alternate pattern of the electrical heat mechanism.

Turning now to FIG. 5, there is shown an electrical heat mechanism 8 that may comprise a solid plate 8*b* rather than the wire snake-patterned coils shown in the previous embodiments. Note that the solid plate may be sectioned as required by the section scheme of the cushioned pad 7. Finally, FIG. 5 also shows a temperature control device 15 which allows a user to control the temperature of the electrical heat mechanism 8 and thus the temperature of the cushioned pad 7. FIG. 6 displays the side elevational view of solid embodiment of the heat mechanism 8*b*.

The specific embodiments discussed in the detailed description are merely illustrative of specific ways to make and use the invention, and do not limit the scope of the invention.

I claim:

1. A foldable, heated massage table comprising, in combination, a sectioned rigid planar surface;

at least one cushioned pad comprising a patient contacting surface placed over a top side of said sectioned surface, where said cushioned pad folds along with said sectioned surface;

an electrical heat mechanism placed within said at least one cushioned pad, wherein said electrical heat mechanism is covered with an insulation material and further wherein said electrical heat mechanism is placed in the middle of the pad, a sufficient distance away from the contacting surface of said cushioned pad and from the top side of the sectioned surface such that a substantially consistent heat is emitted at said contact surface;

a temperature control mechanism; and foldable legs on another side of said side of said surface of said sectioned surface.

2. A foldable, heated massage table as in claim 1 where said cushioned pad is a mattress pad.

* * * * *